US011276487B2

(12) United States Patent
Potts

(10) Patent No.: US 11,276,487 B2
(45) Date of Patent: Mar. 15, 2022

(54) SYSTEMS AND METHODS FOR PROVIDING PRESCRIPTION MEDICATION DELIVERY AND REMINDER SERVICES

(71) Applicant: ScriptDrop, Inc., Nashville, TN (US)

(72) Inventor: Nicholas Potts, Nashville, TN (US)

(73) Assignee: ScriptDrop, Inc., Nashville, TN (US)

( * ) Notice: Subject to any disclaimer, the term of this patent is extended or adjusted under 35 U.S.C. 154(b) by 0 days.

(21) Appl. No.: 16/989,867

(22) Filed: Aug. 10, 2020

(65) Prior Publication Data

US 2020/0372994 A1 Nov. 26, 2020

Related U.S. Application Data

(63) Continuation of application No. 16/398,876, filed on Apr. 30, 2019, now Pat. No. 10,741,276, which is a continuation-in-part of application No. 15/969,663, filed on May 2, 2018.

(Continued)

(51) Int. Cl.
*G16H 40/20* (2018.01)
*G16H 20/13* (2018.01)
(Continued)

(52) U.S. Cl.
CPC ............ *G16H 20/13* (2018.01); *G16H 40/20* (2018.01); *G16H 80/00* (2018.01); *H04L 67/02* (2013.01); *H04L 67/12* (2013.01); *H04L 67/26* (2013.01)

(58) Field of Classification Search
CPC ........ G16H 20/13; G16H 40/20; G16H 80/00; G16H 20/10; G16H 40/67; G16H 10/60;
(Continued)

(56) References Cited

U.S. PATENT DOCUMENTS 5,845,255 A 12/1998 Mayaud
10,289,806 B2 5/2019 Hyde et al.
(Continued)

FOREIGN PATENT DOCUMENTS

| CN | 106456446 A | 2/2017 |
| KR | 1020020061445 A | 7/2002 |
| KR | 1020060087752 A | 8/2006 |

OTHER PUBLICATIONS

Search Report and Written Opinion in corresponding International application No. PCT/US2018/030818, dated Sep. 14, 2018, 12 pages.
(Continued)

*Primary Examiner* — Maroun P Kanaan
(74) *Attorney, Agent, or Firm* — Patterson Intellectual Property Law, P.C.

(57) ABSTRACT

Novel systems, methods, and devices for implementing prescription delivery and for providing medication reminders are provided. One system for providing a prescription medication delivery service operates by a server configured to receive a requested delivery signal including delivery coordinator information and prescription medication information. A physician device receives input relating to a selection of a prescription delivery option within a pharmacy dispensing system and transmits a corresponding request message associated with the prescription delivery option via the communication network. A prescription delivery service server configured receives the request message via the communication network and coordinates delivery of the prescription medication based at least in part upon the delivery coordinator and the prescription medication information.

13 Claims, 6 Drawing Sheets

Related U.S. Application Data

(60) Provisional application No. 62/500,861, filed on May 3, 2017.

(51) Int. Cl.
*H04L 67/02* (2022.01)
*G16H 80/00* (2018.01)
*H04L 67/12* (2022.01)
*H04L 67/55* (2022.01)

(58) Field of Classification Search
CPC ........ G16H 20/00; G16H 70/20; G16H 70/40; G06Q 10/0832; H04L 67/02; H04L 67/12; H04L 67/26
See application file for complete search history.

(56) References Cited

U.S. PATENT DOCUMENTS

| | | | |
|---|---|---|---|
| 2006/0122729 A1 | 6/2006 | Murphy et al. | |
| 2007/0143137 A1* | 6/2007 | Ross | G06F 19/3456 705/2 |
| 2012/0179480 A1 | 7/2012 | Patel et al. | |
| 2015/0134107 A1 | 5/2015 | Hyde et al. | |
| 2015/0371000 A1 | 12/2015 | Pinsonneault | |
| 2016/0292378 A1* | 10/2016 | Saric | G06F 19/3418 |
| 2018/0012176 A1* | 1/2018 | McHale | G06Q 10/0832 |
| 2018/0075215 A1 | 3/2018 | Loiacono et al. | |
| 2018/0253682 A1* | 9/2018 | Gilman | G06Q 10/00 |

OTHER PUBLICATIONS

Google search "directly submitting prescription delivery request to delivery service using identification," dated Feb. 7, 2020, 2 pages, as cited in co-pending U.S. Appl. No. 15/969,663 and provided to Applicant on Feb. 20, 2020.

NCPDP: Testimony to NCVHS, Session A1: Proposals for a National Health Plan Identifier, dated Jul. 19, 2010, 4 pages, as cited in co-pending U.S. Appl. No. 15/969,663 and provided to Applicant on Feb. 20, 2020.

\* cited by examiner

| | |
|---|---|
| 101-A1 | BIN |
| 102-A2 | Version |
| 103-A3 | Transaction Code |
| 104-A4 | Processor Control Number |
| 109-A9 | Transaction Count |
| 110-AK | Software Vendor/Certification ID |
| 111-AM | Segment Identification |
| 201-B1 | Service Provider ID Qualifier |
| 202-B2 | Service Provider ID |
| 301-C1 | Group ID |
| 302-C2 | Cardholder ID |
| 303-C3 | Person Code |
| 304-C4 | Date of Birth |
| 305-C5 | Patient Gender Code |
| 306-C6 | Patient Relationship Code |
| 310-CA | Patient First Name |
| 311-CB | Patient Last Name |
| 322-CM | Patient Street Address |
| 323-CN | Patient City Address |
| 324-CO | Patient State/Province Code |
| 325-CP | Patient Zip/Postal Code |
| 401-D1 | Date of Service |
| 402-D2 | Prescription/Service Reference Number |
| 405-D5 | Days' Supply |
| 407-D7 | Product/Service ID |
| 411-DB | Prescriber ID |
| 427-DR | Prescriber Last Name |
| 436-E1 | Product/Service ID Qualifier |
| 442-E7 | Quantity Dispensed |
| 455-EM | Prescription/Service Reference Number Qualifier |
| 466-EZ | Prescriber ID Qualifier |
| 337-4C | Coordination of Benefits/Other Payments Count |
| 338-5C | Other Payer Coverage Type |
| 353-NR | Other Payer-Patient Responsibility Amount Count |
| 340-7C | Other Payer ID |
| 339-6C | Other Payer ID Qualifier |
| 351-NP | Other Payer-Patient Responsibility Amount Qualifier |
| 352-NQ | Other Payer-Patient Responsibility Amount |
| 433-DX | Patient Paid Amount Submitted |
| 430-DU | Gross Amount Due |
| 403-D3 | Fill Number |
| 415-DF | Number of Refills Authorized |

FIG. 4

SYSTEMS AND METHODS FOR PROVIDING PRESCRIPTION MEDICATION DELIVERY AND REMINDER SERVICES

CROSS-REFERENCES TO RELATED APPLICATIONS

This application claims priority to and the benefit of the following patent applications which are hereby incorporated by reference in their respective entireties. This application is a continuation of U.S. Non-Provisional patent application Ser. No. 16/398,876 filed on Apr. 30, 2019, entitled "Systems and Methods for Providing Prescription Medication Delivery and Reminder Services," which is a continuation-in-part of U.S. Non-Provisional patent application Ser. No. 15/969,663 filed on May 2, 2018, entitled "Systems and Methods for Providing Prescription Medication Delivery and Reminder Services," which claims the benefit of U.S. Provisional Patent Application No. 62/500,861 filed on May 3, 2017, entitled "Systems and Methods for Providing Prescription Medication Delivery and Reminder Services."

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present disclosure relates generally to systems and methods for providing prescription medication delivery and reminder services.

Existing systems for providing prescription medication to end users are cumbersome and suffer problems associated with prescription non-pickup. Prescription delivery services are inefficient from the perspective of pharmacies, as redundant data entry is often required (e.g., once to enter prescription data for a claim, and then again entering the data for delivery). Pharmaceutical companies also experience inefficiency with existing systems, for example in the form of reversals which might lead to excessive losses in potential revenue. Inefficient prescription processes cost health plans significant amounts of money on hospital readmissions due to medication non-adherence. Health plans' star ratings also take a hit based on non-adherence, which can cause issues with future reimbursements for Medicare/Medicaid. In a recent study conducted by CVS Caremark, medication non-adherence cost the entire health care system $290 billion.

Reversals are a serious problem with existing prescription pickup implementations. A reversal occurs when a prescription is approved but the patient never returns to pick up the approved prescription. The pharmacy is then required to run a reversal and return the transaction to the plan in 14 days. Reversals cost the pharmacy money (e.g., in the form of employee overhead, transaction fees, carrying costs, etc.), that the pharmacy ultimately doesn't recoup. Unrealized filled prescriptions cost the Pharmaceutical companies money. Some Pharmaceutical companies are missing out on hundreds of millions of dollars per year on a single brand on just-approved prescriptions that sit on pharmacy shelves and ultimately get reversed.

In view of the foregoing, a need exists to provide systems and methods for implementing a prescription delivery service which eliminates redundancy in data entry for pharmacies while providing a prescription delivery service which also addresses downfalls associated with traditional prescription medication distribution.

BRIEF SUMMARY OF THE INVENTION

Inventions consistent with the present disclosure address holes in the process of getting a patient their medication in a timely and effective manner, and provide novels systems and methods for providing a prescription delivery service.

Scriptdrop is a prescription delivery service that can operate in the workflow of a pharmacist. Scriptdrop offers simplicity by permitting pharmacies to simply bill a custom bank identification number (BIN) number rather than requiring a pharmacist to download a standalone app in one embodiment. This ensures that communications are secure and that the data is encrypted. Pertinent data may be sent to a Scriptdrop server which may enable dispatching a driver to pick up a prescription and to deliver the prescription to the corresponding patient.

Like is the case with pharmacists, there is no need for an end user (e.g., prescription recipient) to download an app. Scriptdrop is capable of negating the need for duplicate data entry to request a delivery (e.g., by requiring the same information to be provided in both a traditional payment form and then re-entered for delivery. Scriptdrop enables standardized delivery service for all pharmacies. Once a prescription is delivered to an end user, an acknowledgment of receipt form may be signed (e.g., via e-signature) and filed (e.g., by e-filing). Scriptdrop can even take the co-pay at the point of delivery.

Services consistent with the present disclosure may, in one embodiment, be provided for free to pharmacies and patients. In one embodiment, a predictive model may be provided to message pharmacists to offer a delivery or not, based on the likelihood of losing a particular patient. The model may be a learning algorithm that increases accurate via learning from additional data points. The learning algorithm may be provided with information relating to reversals in one embodiment.

According to one aspect of the present disclosure, provided is a system for providing a prescription medication delivery service by submitting a prescription delivery request via a communication network to the prescription medication delivery service. The system includes a server configured to receive a requested delivery signal via the communication network, the requested delivery signal including delivery coordinator information and prescription medication information, a physician device configured to receive input relating to a selection of a prescription delivery option within a pharmacy dispensing system and to transmit a corresponding request message associated with the prescription delivery option via the communication network, and a prescription delivery service server configured to receive the request message via the communication network and to coordinate delivery of the prescription medication based at least in part upon the delivery coordinator and the prescription medication information.

The system may include a notification device which receives a medication reminder associated with the requested delivery signal via the communication network and further configured to output a notification based at least in part upon the received medication reminder. The medication reminder may be received at the notification device without a simultaneous requested delivery signal associated with the prescription medication.

The prescription delivery service may obtain a delivery confirmation indication associated with the prescription medication. Coordinating delivery of the prescription medication by the prescription delivery service server may include providing a drone delivery service using a courier.

According to another aspect of the present disclosure, provided is a method of providing a prescription medication delivery service by submitting a prescription delivery request to the prescription medication delivery service via a communication network. The method includes requesting delivery of a prescription medication, the requested delivery identifying delivery coordinator information and prescription medication information, selecting a prescription delivery option based at least in part upon the requested delivery, transmitting a request message to a prescription delivery service server via the communication network, selectively relaying the transmitted request message to the prescription delivery service based at least in part upon the delivery coordinator information, coordinating delivery of the prescription medication by the prescription delivery service server based at least in part upon the selectively relayed transmitted request message, the coordinating delivery including providing at least one set of delivery information to a delivery service, and delivering the prescription medication according to the at least one set of delivery information provided to the delivery service.

The method may further include transmitting a medication reminder associated with the requested delivery to a notification device via the communication network, and providing a notification by the notification device based at least in part upon the transmitted medication reminder. The medication reminder may be provided to the notification device without simultaneously requesting delivery of the prescription medication. Delivering the prescription medication may include obtaining a delivery confirmation indication associated with the prescription medication. Coordinating delivery of the prescription medication by the prescription delivery service may include providing a drone delivery service by a courier.

According to a further aspect of the present disclosure, provided is a method of providing a prescription medication delivery service using delivery provider information associated with the prescription medication delivery service via a communications network. The method includes requesting delivery of a prescription medication by the prescription medication delivery service, billing the prescription medication delivery service, processing the billed prescription medication delivery service using a pharmacy switch, wherein the processing includes transmitting the requested delivery to the prescription medication delivery service via the communication network, coordinating delivery of the prescription medication by the prescription medication delivery service, and delivering the prescription medication according to the requested delivery.

The method further includes transmitting a medication reminder associated with the requested delivery to a notification device via the communication network, and providing a notification by the notification device based at least in part upon the transmitted medication reminder. The medication reminder may be provided to the notification device without simultaneously requesting delivery of the prescription medication. Delivering the prescription medication may include obtaining a delivery confirmation indication associated with the prescription medication. Coordinating delivery of the prescription medication by the prescription delivery service may include providing a drone delivery service by a courier.

Numerous other objects, features, and advantages of the present invention will be readily apparent to those skilled in the art upon a reading of the following disclosure when taken in conjunction with the accompanying drawings.

BRIEF DESCRIPTION OF THE SEVERAL VIEWS OF THE DRAWINGS

FIG. 4 illustrates a listing of payer sheet information consistent with the present disclosure according to an exemplary embodiment.

DETAILED DESCRIPTION OF THE INVENTION

Figure 1:
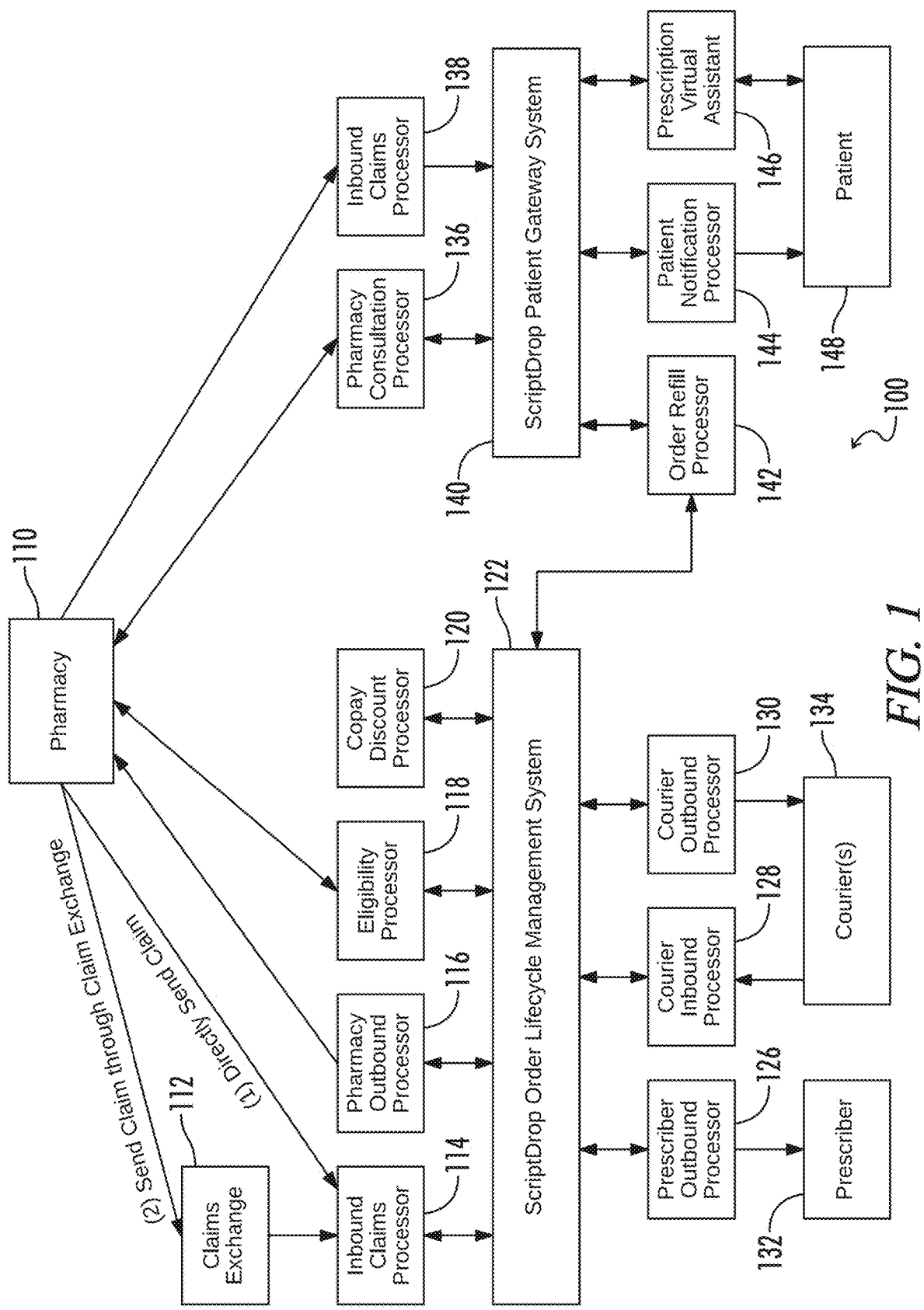
FIG. 1 provides a block diagram illustrating a configuration of a system for providing a prescription delivery service according to an exemplary embodiment.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

Referring generally to FIGS. 1-6, various exemplary apparatuses and associated methods according to the present disclosure are now described in detail. Where the various figures may describe embodiments sharing various common elements and features with other embodiments, similar elements and features are given the same reference numerals and redundant description thereof may be omitted below.

Various embodiments of an apparatus according to the present invention may provide systems and methods for providing prescription delivery and meditation reminder services.

As shown in FIG. 1, in one exemplary embodiment, a prescription delivery system 100 implemented using a pharmacy dispensing system may include a pharmacy 110 communicatively coupled to at least one of a claims exchange 112, an inbound claims processor 114, a pharmacy outbound processor 116, and an eligibility processor 118. A pharmacist associated with the pharmacy 110 may send a claim to at least one of the claims exchange 112 and/or directly to the inbound claims processor 114. When a claim is sent to the claims exchange 112, the claim is processed by the claims exchange 112 and a result of the processing is communicated to the inbound claims processor 114. The inbound claims processor 114 is communicatively coupled to an order lifecycle management system such as the Scriptdrop Order Lifecycle Management System 122).

The Scriptdrop Order Lifecycle Management System 122 is configured to communicatively couple to at least one of the inbound claims processor 114, the pharmacy outbound processor 116, the eligibility processor 118, the copay discount processor 120, the prescriber outbound processor 126, the courier inbound processor 128, and the courier outbound processor 130. The Scriptdrop Order Lifecycle Management System 122 is configured to control and/or coordinate one or more operations associated with the prescription delivery system 100. For example, in one embodiment, the Scriptdrop Order Lifecycle Management System 122 is configured to interconnect one or more of the pharmacy 110, the prescriber 132, and the couriers 134 and to coordinate and/or control one or more operations associated with at least one entity.

One or more of the inbound claims processor 114, the pharmacy outbound processor 116, the eligibility processor 118, the copay discount processor 120, the prescriber outbound processor 126, the courier inbound processor 128, and the courier outbound processor 130 may be implemented by the Scriptdrop Order Lifecycle Management System 122. Additionally or alternatively, at least one of the processors may be located physically and/or logically remotely from the Scriptdrop Order Lifecycle Management System 122. For example, in one exemplary embodiment, at least one of the processors may be implemented by a distributed computing configuration, a cloud service, a remote server, or any other physically and/or logically remote computing entity capable of performing at least one operation associated with the Scriptdrop Order Lifecycle Management System 122. The pharmacy outbound processor 116 may be configured to send information to and receive information from the Scriptdrop Order Lifecycle Management System 122 and to send information associated with one or more claims to the pharmacy 110. The Scriptdrop Order Lifecycle Management System 122 may be further be communicatively coupled to the eligibility processor 118. The eligibility processor 118 may be configured to send information to and receive information from both of the Scriptdrop Order Lifecycle Management System 122 and the pharmacy 110. The Scriptdrop Order Lifecycle Management System 122 may further be communicatively coupled to the copay discount processor 120. The copay discount processor 120 may be configured to send information to and to receive information from the Scriptdrop Order Lifecycle Management System 122. In one exemplary embodiment, the copay discount processor 120 is configured to processor otherwise operate upon one or more sets of data associated with at least one claim. The copay discount processor 120 may be configured to obtain one or more copay discount criteria from at least one of the Scriptdrop Order Lifecycle Management System 122 and a remote provider, such as an insurer database, the pharmacy 110, or any other entity configured to store or otherwise convey at least one copay discount criteria.

The Scriptdrop Order Lifecycle Management System 122 is further communicatively coupled to the prescriber outbound processor 126. The prescriber outbound processor 126 is configured to send information to and to receive information from the Scriptdrop Order Lifecycle Management System 122. The prescriber outbound processor 126 is further configured to provide information to the prescriber 132. For example, the prescriber outbound processor 126 may be configured to provide information to the prescriber 132 relating to at least one claim. The Scriptdrop Order Lifecycle Management System 122 is further communicatively coupled to the courier inbound processor 128 and to the courier outbound processor 130. Each of the courier inbound processor 128 and the courier outbound processor 130 may be configured to send information to and to receive information from the Scriptdrop Order Lifecycle Management System 122. The courier outbound processor 130 may be configured to provide information to at least one of the couriers 134. The information provided to the at least one courier 134 may relate to at least one claim. The courier inbound processor 128 may be configured to receive information from the at least one courier 134. The information received by the courier inbound processor 128 from the at least one courier 134 may include information associated with a claim and/or delivery criteria or information (e.g., courier delivery status information, courier availability information, courier pricing information, or any other set of information regarding a claim, a courier, or a delivery).

The at least one courier 134 may be one or more courier or delivery services in one exemplary embodiment. Additionally or alternatively, the at least one courier 134 may be an automated and/or drone delivery service or provider. The drone delivery service or provider may take the place of a traditional courier or delivery service. In one exemplary embodiment, interaction between the drone delivery service and one or more components described herein may occur via an application programming interface (API) associated with the drone delivery service. For example, in one implementation, the Scriptdrop Order Lifecycle Management System 122 may be configured to intake a request or claim, to log a physical address associated with a patient, and to selectively convert the physical address to a latitude and longitude equivalent location for drone or automated delivery.

In one exemplary embodiment, data transmitted from the pharmacy 110 may be used to initiate a prescription delivery operation. The process may begin by transmitting a claim from the pharmacy 110 to at least one of the claims exchange 112 and the inbound claims processor 114. The claim may be transmitted from the pharmacy 110 to at least one of the claims exchange 112 and the inbound claims processor 114 via an HTTP or HTTPS connection, a secured Virtual Private Network (VPN) tunnel, or any other means of conveying claim data from the pharmacy 110. The claim may be transmitted preferably through a secured and/or private communications medium (although non-secured or non-secured communications mediums may be used if the claims data is adequately protected, for example by encryption). The claim transmission process may be similar to the above Change Healthcare/Relay Health framework. However, inventions consistent with the present disclosure may include a parallel, combined, or alternative option whereby the pharmacy 110 transmits claim data to the inbound claims processor 114, rather than traditional claim processing by the claims exchange 112.

In one exemplary embodiment, a traditional payer sheet may include a Scriptdrop BIN number (e.g., as a primary or secondary payer). The claim may be processed as usual, with the prescription and delivery information provided to the Scriptdrop system for courier dispatch. Additionally or alternatively, a pharmacy 110 may send a request directly to the Scriptdrop system via the inbound claims processor 114, and one or more confirmations may be sent back to the pharmacy 110 (for example, to indicate receipt of the request, to indicate prescription courier dispatch information relating to a courier, a prescription, or a claim, and/or to confirm delivery). This embodiment may provide advantages relating to avoiding rebilling of a Scriptdrop BIN number, while using software of a pharmacy dispensing system to interact directly with Scriptdrop. In one exemplary embodiment, the pharmacy dispensing system is configured to provide a payer sheet directly to the Scriptdrop system, the payer sheet being substantially identical to that submitted to a traditional switch. The pharmacy dispensing system may be configured such that an internet-based post message is transmitted to Scriptdrop, rather than a billing operation of a Scriptdrop BIN number. In one exemplary embodiment, the pharmacy dispensing system is configured with a user-accessible button or hot key configured to send a web post to Scriptdrop.

The prescription delivery system 100 may further include a pharmacy consultation processor 136 and an inbound claims processor 138 communicatively coupled to both the pharmacy 110 and to a ScriptDrop Patient Gateway System 140. The ScriptDrop Patient Gateway System 140 may be communicatively coupled to at least one of an order refill processor 142, a patient notification processor 144, and a prescription virtual assistant 146. The order refill processor 142 may also be communicatively coupled to the ScriptDrop Order Lifecycle Management System 122 (e.g., via a bidirectional connection whereby one or more instructions and/or sets of data may be transferred therebetween). The order refill processor 142 may be configured to coordinate patient refill ordering and/or warnings. The patient notification processor 144 may be configured to communicate one or more notification messages to a patient 148. The one or more notification messages may include, for example, prescription reorder status or instruction information, medication usage reminders, or any other information relating to at least one of a patient and/or medication. A patient 148 may communicate with at least one prescription virtual assistant 146. The prescription virtual assistant may, in one exemplary embodiment, be a portal accessible by the patient 148 to obtain and/or manipulate at least one set of information relating to a prescription. In one embodiment, the prescription virtual assistant 146 is configured to obtain information relating to at least one prescription and to permit monitoring, warnings, notices, re-order information, or any other form of data to be viewed and/or edited by the patient 148 (e.g., using an electronic device associated with the patient 148).

Figure 2:
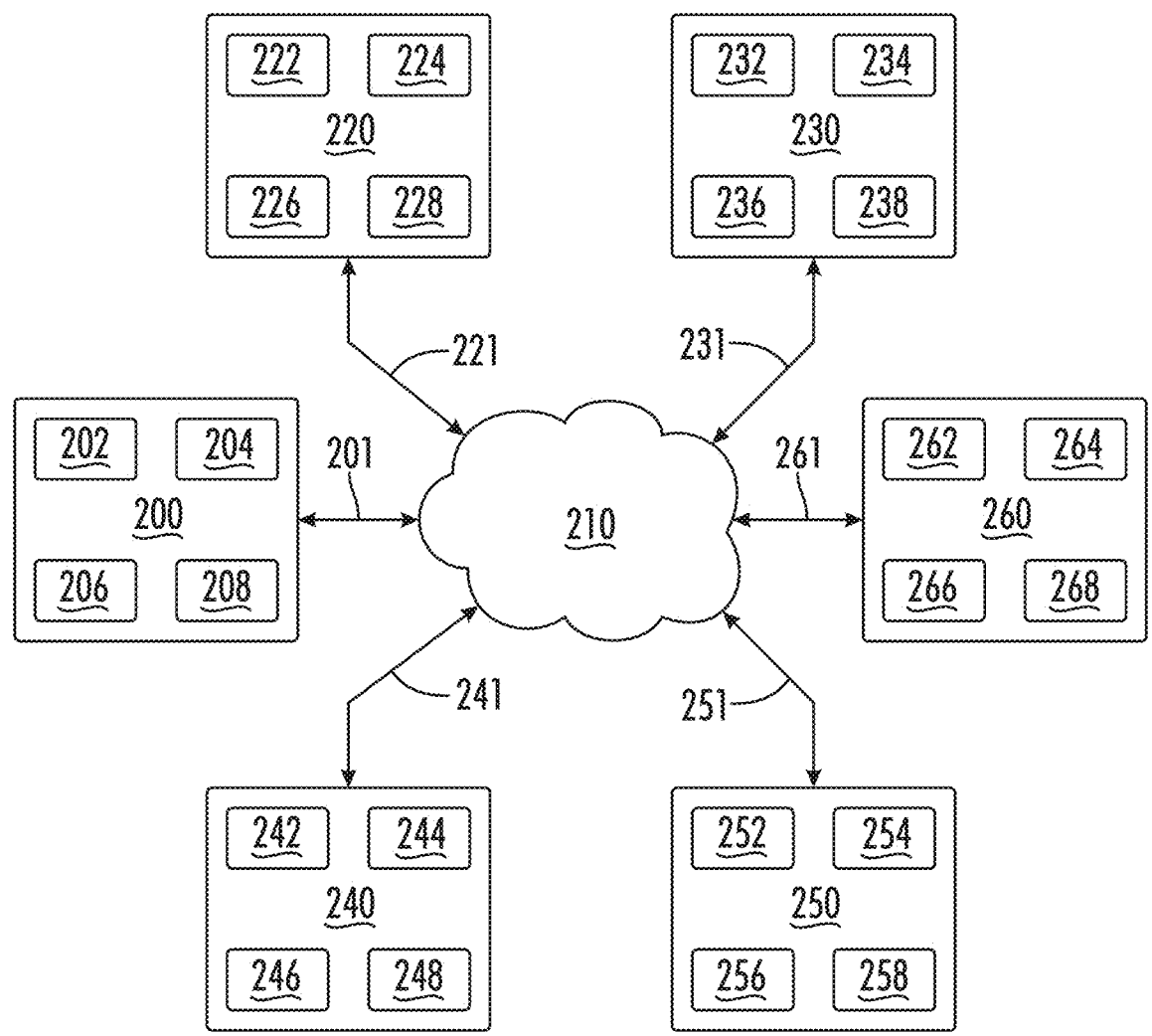
FIG. 2 illustrates an exemplary embodiment of computer system-level implementation consistent with the present disclosure.

FIG. 2 illustrates an exemplary embodiment of computer system-level implementation consistent with the present disclosure. The exemplary embodiment illustrated by FIG. 2 includes an end user electronic device 200. The end user electronic device 200 includes one or more of a microprocessor 202, a storage unit 204, a communications unit 206, and a display unit 208. The communications unit 206 of the end user electronic device 200 is configured to communicate with a network 210 via a communications link 201. In one exemplary embodiment, the network 210 includes the Internet, a public network, a private network, or any other communications network capable of conveying electronic communications.

Connection between the communications unit 206 and network 210 is configured to be performed by wired interface, wireless interface, or a combination thereof, without departing from the spirit and the scope of the present disclosure. In one exemplary operation, the end user electronic device 200 stores one or more sets of instructions in the storage unit 204, which are configured to be executed by the microprocessor 202 to perform operations corresponding to the one or more sets of instructions. The display unit 208 is embodied within the end user electronic device 200 in one embodiment, and is configured to be either wired or wirelessly-interfaced with the end user electronic device 200.

In various exemplary embodiments, the end user electronic device 200 takes the form of at least one of a desktop computer, a laptop computer, a smart phone, or any other electronic device capable of executing instructions. The microprocessor 202 is configured to take the form of a generic hardware processor, a special-purpose hardware processor, or a combination thereof. In embodiments having a generic hardware processor (e.g., as a central processing unit (CPU) available from manufacturers such as Intel and AMD), the generic hardware processor is configured to be converted to a special-purpose processor by means of being programmed to execute and/or by executing a particular algorithm in the manner discussed herein for providing one or more specific operations or results.

The end user electronic device 200 is configured in various embodiments to be associated with a fixed location, but is also capable of being transported, either during operation or while powered off. In one embodiment where the end user electronic device 200 is a client's cellular telephone, the end user electronic device 200 is at least temporarily located at a client's premises. In various embodiments, the end user electronic device 200 is configured to operate remotely, and is configured to obtain or otherwise operate upon one or more instructions stored physically remote from the end user electronic device 200 (e.g., via client-server communications and/or cloud-based computing).

The exemplary embodiment illustrated by FIG. 2 includes at least one pharmacy device 220. Each pharmacy device 220 is configured to connect to the network 210 via the communications link 221 and includes at least one of a microprocessor 222, a storage unit 224, a communications unit 226, and a display unit 228. Each of the microprocessor 222, the storage unit 224, the communications unit 226, and the display unit 228 is configured to respectively correspond to the previously-described microprocessor 202, the storage unit 204, the communications unit 206, and the display unit 208 without departing from the spirit and the scope of the present disclosure.

Each pharmacy device 220 is configured in various embodiments to be associated with a fixed pharmacy location, but is also capable of being transported, either during operation or while powered off. In one embodiment, one or more pharmacy devices 220 is configured to be located at a fixed location and comprises desktop computer configured to receive input from a pharmacist regarding one or more prescriptions and/or claims. One or more pharmacy devices 220 may have stored therein or otherwise have access to a pharmacy dispensing system executable thereon or therewith to perform one or more pharmacy and/or claim operations. In various embodiments, the pharmacy device 220 is configured to operate remotely, and is additionally configured to obtain or otherwise operate upon one or more instructions stored physically remote from the pharmacy device 220 (e.g., via client-server communications and/or cloud-based computing).

One or more prescriber devices 230 consistent with the present disclosure are provided by electronic devices in one exemplary embodiment. Each prescriber device 230 is configured to connect to the network 210 via the communications link 231 and includes at least one of a microprocessor 232, a storage unit 234, a communications unit 236, and a display unit 238. Each of the microprocessor 232, the storage unit 234, the communications unit 236, and the display unit 238 are configured to correspond to the previously-described microprocessor 202, the storage unit 204, the communications unit 206, and the display unit 208 without departing from the spirit and the scope of the present disclosure.

Each prescriber device 230 is configured in various embodiments to be associated with a fixed location, but is also capable of being transported, either during operation or while powered off. In one embodiment, one or more prescriber devices 230 are configured to be located at a fixed location and to comprise a desktop computer. In one exemplary embodiment, at least one of the one or more prescriber devices 230 comprises a moveable laptop or tablet computer. In various embodiments, each prescriber device 230 is configured to operate remotely, and is also configured to obtain or otherwise operate upon one or more instructions stored physically remote from the prescriber device 230 (e.g., via client-server communications and/or cloud-based computing). Each prescriber device 230 may be configured to receive prescription information from a prescriber (e.g., a doctor or other individual with the ability to write prescriptions) and to convey the prescription information to a pharmacy switch and/or pharmacy 110.

In one exemplary embodiment, one or more claims exchange servers 240 (e.g., pharmacy switches) consistent with the present disclosure are provided by one or more electronic devices. In one exemplary embodiment, the one or more claims exchange servers 240 are associated with one or more providers of pharmacy claim switch and billing services. Each claims exchange server 240 is configured to connect to the network 210 via the communications link 241 and is configured to include at least one of a microprocessor 242, a storage unit 244, a communications unit 246, and a display unit 248. Each of the microprocessor 242, the storage unit 244, the communications unit 246, and the display unit 248, in one exemplary embodiment, corresponds to the previously-described microprocessor 202, storage unit 204, communications unit 206, and/or display unit 208, without departing from the spirit and the scope of the present disclosure.

One or more claims exchange servers 240 may be configured to operate as a standalone server, as a distributed server, as a cloud service-based server, or any other configuration capable of executing or otherwise implementing at least one action associated with a claims exchange provider. When implemented in a distributed manner, one or more of the claims exchange servers 240 may be connected to the network 210 and/or to a separate (e.g., private) network. In various embodiments, at least one claims exchange server 240 is configured to operate remotely, and is configured to obtain or otherwise operate upon one or more instructions stored physically remote from the claims exchange server 240 (e.g., via client-server communications and/or cloud-based computing).

In one exemplary embodiment, one or more courier devices 250 consistent with the present disclosure are provided by one or more electronic devices. In one exemplary embodiment, the one or more courier devices 250 are associated with one or more providers of courier or delivery services. Each courier device 250 is configured to connect to the network 210 via the communications link 251 and is configured to include at least one of a microprocessor 252, a storage unit 254, a communications unit 256, and a display unit 258. Each of the microprocessor 252, the storage unit 254, the communications unit 256, and the display unit 258, in one exemplary embodiment, corresponds to the previously-described microprocessor 202, storage unit 204, communications unit 206, and/or display unit 208, without departing from the spirit and the scope of the present disclosure.

One or more courier devices 250 may be configured to operate as a standalone server, as a distributed server, as a cloud service-based server, or any other configuration capable of executing or otherwise implementing at least one action associated with a courier or delivery service provider. When implemented in a distributed manner, one or more of the courier devices 250 may be connected to the network 210 and/or to a separate (e.g., private) network. In various embodiments, at least one claims exchange server 240 is configured to operate remotely, and is configured to obtain or otherwise operate upon one or more instructions stored physically remote from the courier device 250 (e.g., via client-server communications and/or cloud-based computing). Although illustrated as a single device, it should be appreciated that the courier device 250 may include one or more courier devices 250, either standalone or communicatively coupled to one another, configured to perform operations associated with the couriers 134 described herein. Although not illustrated, the one or more courier devices 250 may include a smartphone, tablet PC, or laptop associated with one or more courier or delivery drivers, where the one or more courier or delivery drivers may be assigned to deliver a prescription medication based on at least one claim transmitted from the pharmacy 110.

In one exemplary embodiment, one or more Scriptdrop servers 260 consistent with the present disclosure are provided by one or more electronic devices. In one exemplary embodiment, the one or more Scriptdrop servers 260 may be configured to provide one or more operations or processing associated with at least one of the Scriptdrop Order Lifecycle Management System 122 and/or one or more of the inbound claims processor 114, the pharmacy outbound processor 116, the eligibility processor 118, the copay discount processor 120, the prescriber outbound processor 126, the courier inbound processor 128, and/or the courier outbound processor 130. Additionally or alternatively, the one or more Scriptdrop servers 260 may be configured to provide one or more operations or processing associated with at least one of the Scriptdrop Patient Gateway System 140 and/or one or more of the pharmacy consultation processor 136, the inbound claims processor 138, the order refill processor 142, the patient notification processor 144, and/or the prescription virtual assistant 146.

Each Scriptdrop server 260 is configured to connect to the network 210 via the communications link 261 and is configured to include at least one of a microprocessor 262, a storage unit 264, a communications unit 266, and a display unit 268. Each of the microprocessor 262, the storage unit 264, the communications unit 266, and the display unit 268, in one exemplary embodiment, corresponds to the previously-described microprocessor 202, storage unit 204, communications unit 206, and/or display unit 208, without departing from the spirit and the scope of the present disclosure.

One or more Scriptdrop servers 260 may be configured to operate as a standalone server, as a distributed server, as a cloud service-based server, or any other configuration capable of executing or otherwise implementing at least one action associated with a claims exchange provider. When implemented in a distributed manner, one or more of the Scriptdrop servers 260 may be connected to the network 210 via communications link 261 and/or to a separate (e.g., private) network. In various embodiments, at least one Scriptdrop server 260 is configured to operate remotely, and is configured to obtain or otherwise operate upon one or more instructions stored physically remote from the Scriptdrop server 260 (e.g., via client-server communications and/or cloud-based computing).

Figure 3:
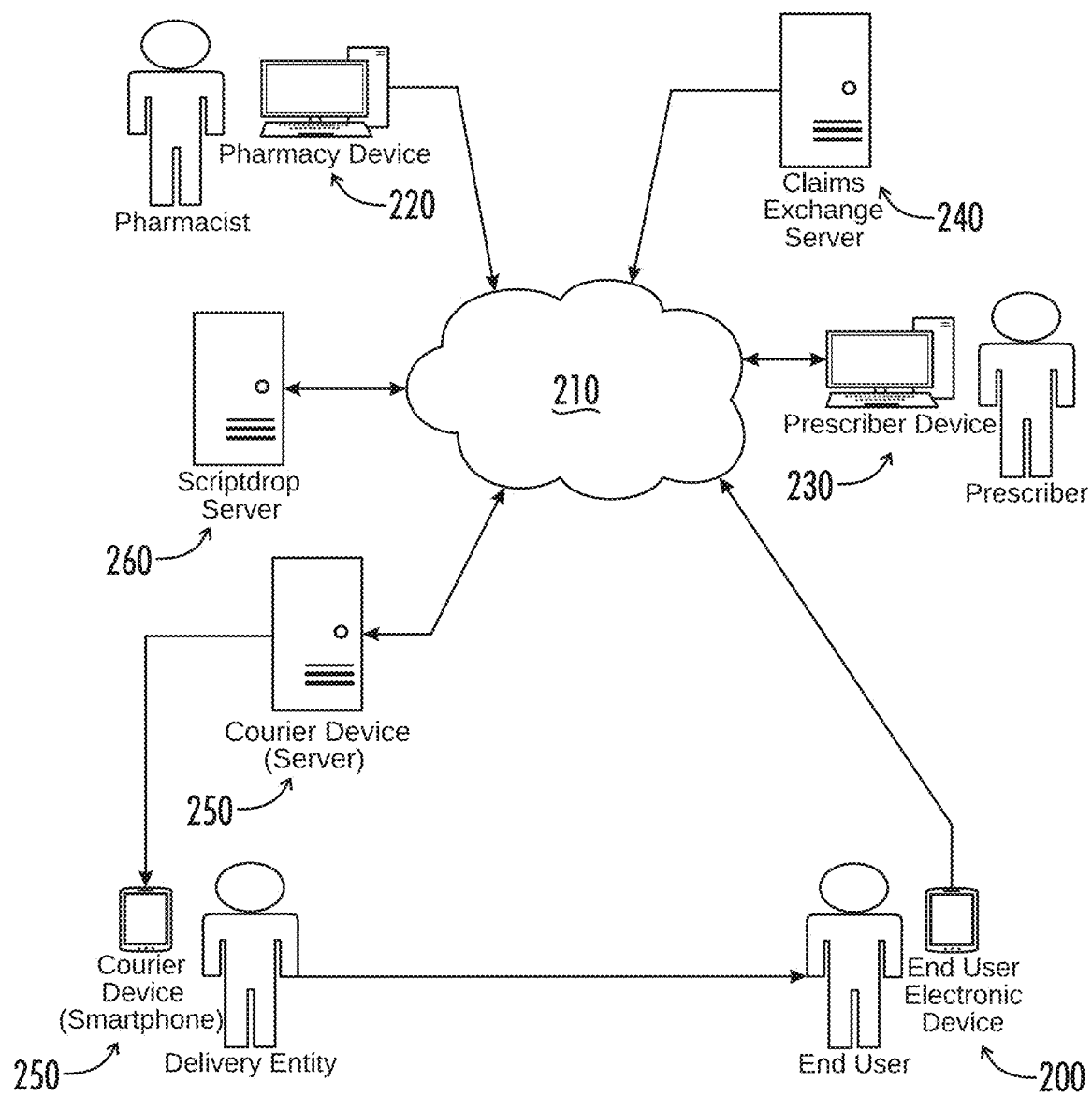
FIG. 3 illustrates a network-level diagram illustrating the relationship between the end user electronic device, the network, the pharmacy device, the prescriber device, the claims exchange server, the courier device(s), and the Scriptdrop server illustrated by FIG. 2.

FIG. 3 illustrates a network-level diagram illustrating the relationship between the end user electronic device 200, the network 210, the pharmacy device 220, the prescriber device 230, the claims exchange server 240, the courier device(s) 250, and the Scriptdrop server 260 as illustrated by and described above with reference to FIG. 2.

FIG. 4 illustrates a listing of payer sheet information consistent with the present disclosure according to an exemplary embodiment. Although the exemplary payer sheet information contains a plurality of specific sets of information, it should be appreciated that one or more sets of information and/or associated codes may be added, modified, or removed from the plurality of specific sets of information without departing from the spirit and the scope of the present disclosure. In one exemplary embodiment, the payer sheet information illustrated by FIG. 4 may be used to inform pharmacists what prescription details are needed to handle a delivery request. One or more claims sent from the pharmacy 110 may include at least a portion of the plurality of specific sets of information.

Figure 5:
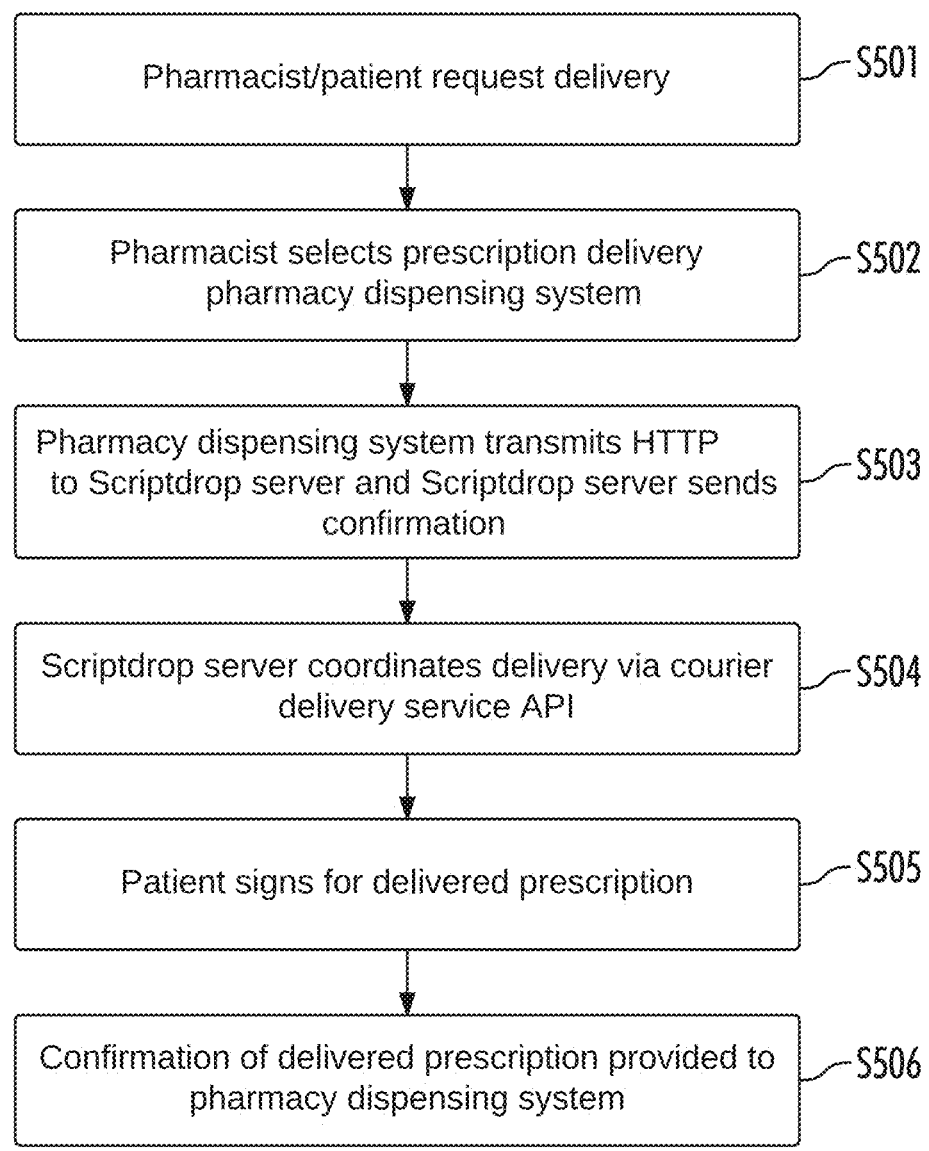
FIG. 5 is a flowchart illustrating a method of providing a prescription delivery operation via direct request from a pharmacy to the prescription delivery service according to an exemplary embodiment.

FIG. 5 is a flowchart illustrating a method of providing a prescription delivery operation via direct request from a pharmacy to the prescription delivery service according to an exemplary embodiment. The process 500 begins at a step S501, where a pharmacist and/or patient requests delivery of a prescription medication from the pharmacist to the patient. The process continues to a step S502, where the pharmacist selects a prescription delivery option within pharmacy dispensing system software. In response to the pharmacist delivery selection, the pharmacy dispensing system transmits an HTTP post message to a Scriptdrop server and the Scriptdrop server responds with a confirmation at a step S503. At a step S504, the Scriptdrop server coordinates delivery of the prescription to the patient using a courier or delivery service application programming interface (API). The prescription is delivered to the patient and the patient signs for the delivered prescription at a step S505. The process concludes at a step S506, where confirmation of the delivered prescription is provided to the pharmacy dispensing system.

Figure 6:
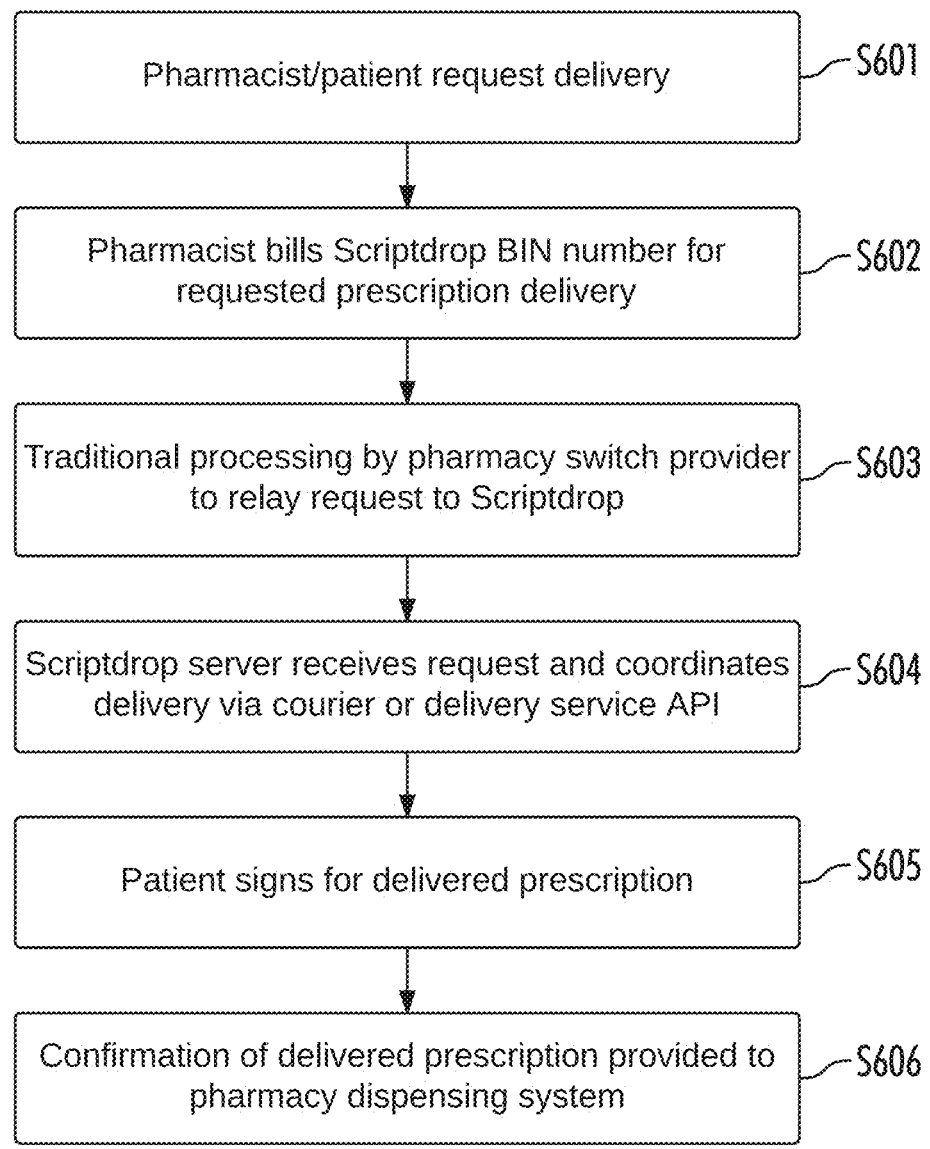
FIG. 6 provides a flowchart illustrating a method of providing a prescription delivery operation via a pharmacy switch to the prescription delivery service according to an exemplary embodiment.

FIG. 6 provides a flowchart illustrating a method of providing a prescription delivery operation via a pharmacy switch to the prescription delivery service according to an exemplary embodiment. The process 600 begins at a step S601, where a pharmacist and/or patient requests delivery of a prescription medication. The process continues to a step S602, where the pharmacist bills Scriptdrop via a predetermined BIN number associated with Scriptdrop. The traditional billing method conveys the bill from the pharmacist to a pharmacy switch, which relays the request to Scriptdrop at a step S603. At a step S604, the Scriptdrop server receives the request and coordinates delivery of the prescription from the pharmacist to the patient via a courier or a delivery service API. The prescription is delivered to the patient and the patient signs for the delivered prescription at a step S605. The process concludes at a step S606, where confirmation of the delivered prescription is provided to the pharmacy dispensing system.

In one exemplary embodiment, implementing the HTTP post message may be done with a direct integration between ScriptDrop and a pharmacy system. This may be based off the NCPDP standard for a B1 or S1 transaction. The BIN process may be performed using one or more of the pharmacy switches. ScriptDrop may integrate with them directly and information regarding the one or more pharmacy switches may be included on a payer sheet. The payer sheet is a document that outlines the data needed to complete a transaction in one embodiment. It is also based off of the NCPDP standard for B1 or S1 transactions. Through this process, ScriptDrop, for all intents and purposes, may be viewed as the health plan. A pharmacist "bills" a ScriptDrop BIN to see if ScriptDrop can deliver the specific prescription or kick off a medication reminder for that patient. ScriptDrop may then respond back to the pharmacist through the pharmacy switch.

One aspect of the present disclosure relates to providing systems and methods for sending data from a pharmacy switch (e.g., Change Healthcare or Relay Health) to initiate a prescription delivery process by billing or rebilling a BIN number. This is the same process for a pharmacist to bill a health plan. In one exemplary embodiment, the prescription delivery service has a registered National Council for Prescription Drug Programs (NCPDP) BIN number which is used in the delivery initiation process. Payer sheet information may be sent to a pharmacy switch provider (e.g., Change Healthcare) for use with the present disclosure (e.g., as illustrated by FIG. 4). The payer information sheet may tell pharmacists what prescription details used to handle a delivery request.

In another aspect of the present disclosure, systems and methods for providing medication reminders to user devices is provided. In various embodiments, the user device may include an Amazon Echo, a Google Home, a text message, and electronic mail message, an automated telephone call, or any other means of conveying information to a user. In providing medication reminders, implementations consistent with the present disclosure may leverage data already available at the pharmacy. In contrast to existing reminder apps which require the patient to enter the data, the data and associated reminders may be created and/or maintained by at least one of the pharmacy, the prescriber, and/or the patient, thereby adding convenience, oversight, and reliability.

In one exemplary embodiment, a medication reminder process may include the steps of receiving a request or claim in the traditional manner described above (e.g., by billing a particular BIN number with payer sheet details). The process continues by searching a database to determine if a patient associated with the request or claim has downloaded application software capable of providing one or more notifications. If there is a match between the patient and the application software, one or more notifications and/or associated configuration data may be provided to a device associated with the patient to convey notifications to the patient in accordance with the one or more notifications and/or associated configuration data. If there is not a match between the patient and the application software in the database, the patient may be asked to download the application software, and actionable electronic communications may be provided to a patient device for downloading the application software (e.g., via a text message or e-mail message), or a combination thereof. The patient may then download the application software for use with the medication reminder system. In using the medication reminder system, once a patient has downloaded the application software to a device, at least one of the patient, a pharmacist, a prescriber, an insurance company, or any other individual or entity associated with a particular prescription or patient may select or change a setting for the patient to receive reminders via one or more devices or means of communication. For example, a patient may have registered to receive text message reminders, but may either switch the notifications to later receive the reminders via a separate device, such as a Google Home, an Amazon Echo, a new smartphone, etc.

In another aspect of the present disclosure, prescription data may be sent to a smart pillbox as opposed to a courier. In this embodiment, one or more sets of prescription data may be transmitted from the pharmacy and may be received at a user's smart pill box (not illustrated). Upon receipt, the smart pill boxes may perform one or more operations corresponding to the received prescription data. Operations may include for example, scheduling pill availability, scheduling pill reminders, modifying an existing pill schedule, or any other operation associated with the prescription, the smart pill box, or the user.

Smart pillbox implementations may operate similar to medication reminders as described above. In one smart pillbox implementation, a patient may possess or have access to a smart pillbox and an identifier of at least one of the patient and the smart pillbox may be stored in a database. For example, a database associated with a Scriptdrop server may store or have access to information linking a particular smart pillbox to a particular patient. When an intake request or claim is received, Scriptdrop knows that the pillbox has been replenished, and thus appropriate information may be sent to at least one of the smart pillbox and application software associated with the patient. In one exemplary embodiment, a smart pillbox may be Bluetooth-enabled and be communicatively coupleable to a device associated with the patient (e.g., a smartphone or tablet). When the patient opens the smart pillbox to take a medication, a push notification may be provided to or by the application software on the patient device with a picture of one or more pills to be taken by the patient.

The smart pillbox may be configured to use the same framework as both the delivery request and the medication reminder request. In one exemplary embodiment, rather than sending the data to a courier, drone, or medication reminder device, the data may be sent to a smart pillbox (e.g., via the user's phone, a communication module associated therewith, or any other means of communication or data entry). The smart pillbox may be associated with the user's phone or device, for example by an app that the user has downloaded through Bluetooth or other communications protocol. When the user receives prescription data as described herein, the smart pillbox may be updated by virtue of a Wi-Fi connection and/or the user's phone. The user may open the smart pillbox and one or more push notifications may be provided to the user via their phone. A push notification may include information regarding a pill that the user is scheduled to take in one embodiment. For example, a user may be provided with one or more of a picture of a pill and/or any dosing instructions. With the smart pillbox being connected to the user's device, it may be determined when a smart pillbox is opened, and notifications can be handled accordingly. In one exemplary embodiment, when the user responds to a push notification, the smart pillbox may be configured to update its pill count. This may also be tied to the user's downloaded application software and/or a medication reminder service. If the user has access to an electronic device such as an Amazon Echo, Google Home, or the like, a current pill quantity may be updated there as well, and or communicated to another entity.

In one exemplary embodiment, Scriptdrop has one or more registered and/or predetermined BIN numbers from at least one database (e.g., one or more NCPDP BIN numbers) that may be used by a pharmacist to request a prescription delivery. Once the pharmacist bills to the one or more BIN numbers the pharmacy sends all the data required for use in the transaction. As such, no duplicate data entry is needed because insurance has already been billed using the same information.

Implementation according to an exemplary embodiment optionally may begin with a patient causing a prescription to be sent to a pharmacy (e.g., either directly or indirectly in association with a provider insurer, or any other healthcare, insurance or other entity). The prescription and/or data associated with the prescription may be transmitted, in whole or in part, via one or more electronic messages transmitted across one or more wired and/or wireless communication networks. The pharmacy may transmit NCPDP-formatted information relating to the prescription to the ScriptDrop system (e.g., as a claim or claim data in various embodiments previously described herein). The ScriptDrop system may selectively create a delivery order and may transmit a delivery order or other delivery or prescription information (such as order scheduling information) to a courier delivery management system.

The courier delivery management system may then send a delivery order or other delivery or prescription information to a courier and/or third-party vendor. In various embodiments, the ScriptDrop system may query real-time or pre-determined quote information from one or a plurality of couriers or other delivery entities, either prior to scheduling a courier delivery, at one or more steps of the processes described herein, or may selectively not obtain quotes from any courier or entity.

A courier may be dispatched to the pharmacy to obtain the physical prescription (e.g., based at least in part upon an electronic message transmitted from the courier service to the courier, such as by electronic message to a computing device of the courier). The courier may then deliver the physical prescription to the patient, and may selectively obtain the patient's signature or other completed or secured delivery option (such as a courier ensuring the identity of the receiving entity, etc.). The courier delivery management system may then transmit the signature or other verification data to the ScriptDrop system (e.g., via one or more system databases).

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims. The phrase "in one embodiment," as used herein does not necessarily refer to the same embodiment, although it may.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The previous detailed description has been provided for the purposes of illustration and description. Thus, although there have been described particular embodiments of a new and useful invention, it is not intended that such references be construed as limitations upon the scope of this invention except as set forth in the following claims.

What is claimed is:

1. A system for providing a prescription medication delivery service by submitting a prescription delivery request via a communication network to the prescription medication delivery service, the system comprising:
   a server configured to receive a requested delivery signal via the communication network, the requested delivery signal including delivery coordinator information and prescription medication information;
   a prescriber device configured to receive input relating to a selection of a prescription delivery option within a pharmacy dispensing system and to transmit a corresponding request message associated with the prescription delivery option to a switch via the communication network, the request message including billing information associated with the prescription delivery service as part of a claim or transaction; and
   a prescription delivery service server configured to receive the request message via the communication network and to coordinate delivery of the prescription medication based at least in part upon the delivery coordinator and the prescription medication information and information contained in the claim or transaction via an Application Programming Interface (API) associated with a courier or a delivery service.

2. The system of claim 1, further comprising:
   a notification device configured to receive a medication reminder associated with the requested delivery signal via the communication network and further configured to output a notification based at least in part upon the received medication reminder.

3. The system of claim 2, wherein the medication reminder is received at the notification device without a simultaneous requested delivery signal associated with the prescription medication.

4. The system of claim 1, wherein the prescription delivery service is configured to obtain a delivery confirmation indication associated with the prescription medication.

5. The system of claim 1, wherein the coordinating delivery of the prescription medication by the prescription delivery service server includes providing a drone delivery service using a courier.

6. A method of providing a prescription medication delivery service by submitting a prescription delivery request to the prescription medication delivery service via a communication network, the method comprising:
   requesting delivery of a prescription medication, the requested delivery identifying delivery coordinator information and prescription medication information;
   selecting a prescription delivery option based at least in part upon the requested delivery;
   transmitting a request message to a prescription delivery service server via the communication network, the request message including billing information associated with the prescription delivery service as part of a claim or transaction;
   selectively relaying the transmitted request message to the prescription delivery service based at least in part upon the delivery coordinator information;
   coordinating delivery of the prescription medication by the prescription delivery service server based at least in part upon the selectively relayed transmitted request message, the coordinating delivery including providing at least one set of delivery information and at least a portion of information contained in the claim or transaction to a delivery service information via an Application Programming Interface (API) associated with the delivery service; and
   delivering the prescription medication according to the at least one set of delivery information provided to the delivery service.

7. The method of claim 6, further comprising:
   transmitting a medication reminder associated with the requested delivery to a notification device via the communication network; and
   providing a notification by the notification device based at least in part upon the transmitted medication reminder.

8. The method of claim 7, wherein the medication reminder is provided to the notification device without simultaneously requesting delivery of the prescription medication.

9. The method of claim 6, wherein the delivering the prescription medication includes obtaining a delivery confirmation indication associated with the prescription medication.

10. The method of claim 6, wherein the coordinating delivery of the prescription medication by the prescription delivery service includes providing a drone delivery service by a courier.

11. The system of claim 1, wherein the switch is a pharmacy switch.

12. The system of claim 1, wherein the claim or transaction is a payer sheet.

13. The system of claim 1, wherein the switch is a pharmacy switch and the claim or transaction is a payer sheet.

* * * * *